(12) United States Patent
Bral

(10) Patent No.: US 10,933,199 B2
(45) Date of Patent: *Mar. 2, 2021

(54) MEANS AND METHOD TO GIVE INJECTIONS WITH LITTLE OR NO PAIN

(71) Applicant: Pourang Bral, Passaic, NJ (US)

(72) Inventor: Pourang Bral, Passaic, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/731,704

(22) Filed: Jul. 19, 2017

(65) Prior Publication Data

US 2019/0184112 A1    Jun. 20, 2019

Related U.S. Application Data

(63) Continuation of application No. 12/590,658, filed on Nov. 12, 2009, now Pat. No. 9,770,560.

(51) Int. Cl.
*A61M 5/42* (2006.01)
*A61N 1/05* (2006.01)
*A61N 1/36* (2006.01)

(52) U.S. Cl.
CPC .......... *A61M 5/422* (2013.01); *A61N 1/0502* (2013.01); *A61N 1/36021* (2013.01); *A61M 2205/3606* (2013.01)

(58) Field of Classification Search
CPC .......... A61M 5/422; A61M 5/3287; A61M 2209/088; A61N 1/0456; A61N 1/36021; A61H 15/0092
See application file for complete search history.

(56) References Cited

U.S. PATENT DOCUMENTS

| | | | |
|---|---|---|---|
| 1,561,116 A | 11/1925 | Silliman | |
| 2,258,857 A | 11/1941 | McCann | |
| 2,945,496 A | 7/1960 | Fosdal | |
| 3,207,159 A | 9/1965 | Tateisi | |
| 3,308,823 A | 3/1967 | Peterson | |
| 3,467,104 A | 9/1969 | Burbridge | |
| 3,620,209 A | 11/1971 | Karvitz | |
| 3,626,929 A | 12/1971 | Sanz et al. | |
| 3,971,229 A | 7/1976 | Privas | |
| 4,046,142 A * | 9/1977 | Whitney | A61H 7/005 601/108 |
| 4,243,035 A | 1/1981 | Barrett | |
| 4,309,989 A | 1/1982 | Fahim | |
| 4,440,167 A | 4/1984 | Takehisa | |

(Continued)

FOREIGN PATENT DOCUMENTS

| | | |
|---|---|---|
| JP | 01-185245 A | 7/1989 |
| JP | 07-051251 | 2/1995 |

(Continued)

OTHER PUBLICATIONS

International Search Report for PCT/JP03/11006, dated Oct. 28, 2003, (with English translation).
https://en.wikipedia.org/wiki/Refractory_Period_(Physiology).

*Primary Examiner* — Laura A Bouchelle

(57) ABSTRACT

A preferred method to obtain a painless or near painless needle 8 penetration is disclosed to be in the following manner: Applying electric current using a TENS device in conjunction with physically stimulating the injection site at a frequency that is dependent on the frequency of the electric current applied to the injection site, followed by a needle 8 penetration into the skin 2.

20 Claims, 8 Drawing Sheets

(56) References Cited

U.S. PATENT DOCUMENTS

| | | |
|---|---|---|
| 4,676,257 A | 6/1987 | Halpern |
| 4,701,167 A | 10/1987 | Chekan |
| 4,710,172 A | 12/1987 | Jacklich et al. |
| 4,725,265 A | 2/1988 | Sairenji |
| 4,900,721 A | 2/1990 | Bansemir |
| 4,924,880 A | 5/1990 | O'Neill |
| 5,035,704 A | 7/1991 | Lambert |
| 5,088,925 A | 2/1992 | Mason |
| 5,171,225 A | 12/1992 | Sterrett |
| 5,271,522 A | 12/1993 | Ko |
| 5,431,655 A | 7/1995 | Melker |
| 5,437,606 A | 8/1995 | Tsukamoto |
| 5,496,363 A | 3/1996 | Burgio |
| 5,578,014 A | 11/1996 | Erez |
| 5,647,851 A | 7/1997 | Pokras |
| 5,680,872 A | 10/1997 | Sesekura et al. |
| 5,728,050 A | 3/1998 | Lin |
| 5,730,753 A | 3/1998 | Morita |
| 5,839,895 A | 11/1998 | Fishburne |
| 5,857,983 A | 1/1999 | Douglas et al. |
| 5,873,844 A | 2/1999 | Campero |
| 5,873,887 A | 2/1999 | King et al. |
| 5,891,053 A | 4/1999 | Sesekura |
| 5,899,880 A | 5/1999 | Bellhouse |
| 5,927,976 A | 7/1999 | Wu |
| 5,954,738 A | 9/1999 | LeVaughn et al. |
| 5,964,718 A | 10/1999 | Duchon et al. |
| 6,045,567 A | 4/2000 | Taylor et al. |
| 6,063,039 A | 5/2000 | Cunningham et al. |
| 6,066,103 A | 5/2000 | Duchon et al. |
| 6,099,503 A | 8/2000 | Stradella |
| 6,135,769 A | 10/2000 | Kwan |
| 6,155,992 A | 12/2000 | Henning et al. |
| 6,200,308 B1 | 3/2001 | Pope |
| 6,217,561 B1 | 4/2001 | Gibbs |
| 6,231,531 B1 | 5/2001 | Lum |
| 6,419,490 B1 | 7/2002 | Weathers |
| 6,454,743 B1 | 9/2002 | Weber |
| 6,547,561 B2 | 4/2003 | Meller |
| 6,599,272 B1 | 7/2003 | Hjertman |
| 6,602,229 B2 | 8/2003 | Coss |
| 6,626,887 B1 | 9/2003 | Wu |
| 6,660,029 B2 | 12/2003 | VanSkiver |
| 6,706,000 B2 | 3/2004 | Perez et al. |
| 6,708,060 B1 | 3/2004 | Avrahami |
| 6,902,554 B2 | 6/2005 | Huttner |
| 7,386,349 B2 | 6/2008 | Davar |
| 7,803,128 B2 | 9/2010 | Christensen |
| 8,500,678 B1 | 8/2013 | Leibovici |
| 8,998,842 B2 | 4/2015 | Lauchard |
| 9,770,560 B2 * | 9/2017 | Bral .................. A61M 5/422 |
| 2001/0049510 A1 | 12/2001 | Burr |
| 2002/0082522 A1 | 6/2002 | Douglas |
| 2002/0128600 A1 | 9/2002 | Nissels |
| 2002/0147446 A1 | 10/2002 | Ein-Gal |
| 2002/0188223 A1 | 12/2002 | Perez et al. |
| 2002/0193861 A1 | 12/2002 | Harrison |
| 2003/0036034 A1 | 2/2003 | Kay |
| 2003/0078534 A1 | 4/2003 | Hochman |
| 2003/0100888 A1 | 5/2003 | Spinello |
| 2004/0015188 A1 | 1/2004 | Coulter |
| 2004/0092843 A1 | 5/2004 | Kreiser et al. |
| 2004/0230227 A1 | 11/2004 | Avrahami |
| 2005/0177071 A1 | 8/2005 | Nakayama |
| 2005/0177201 A1 | 8/2005 | Freeman |
| 2006/0030824 A1 | 2/2006 | Hunn |
| 2006/0106363 A1 | 5/2006 | Aravena et al. |
| 2006/0173386 A1 | 8/2006 | Lindquist |
| 2006/0217636 A1 | 9/2006 | Braig |
| 2007/0088385 A1 | 4/2007 | Perry |
| 2007/0197968 A1 | 8/2007 | Pongpairochana |
| 2007/0282400 A1 * | 12/2007 | Gorham .................. A61B 18/04 607/88 |
| 2008/0039829 A1 | 2/2008 | Goldman |
| 2008/0125842 A1 | 3/2008 | Petitt |
| 2008/0109049 A1 * | 5/2008 | Schumann .......... A61H 39/002 607/46 |
| 2008/0188779 A1 * | 8/2008 | Vallero ................ A61M 5/422 601/21 |
| 2009/0004628 A1 | 1/2009 | Knutson |
| 2009/0118789 A1 | 5/2009 | Buhlmann |
| 2010/0030299 A1 | 2/2010 | Covalin |
| 2011/0022115 A1 * | 1/2011 | Salzhauer ............ A61H 1/005 607/46 |

FOREIGN PATENT DOCUMENTS

| | | |
|---|---|---|
| JP | 07-255706 | 10/1995 |
| JP | 08-187237 | 7/1996 |
| JP | 08-317917 | 12/1996 |
| JP | 08-317918 | 12/1996 |
| JP | 10-127610 | 5/1998 |
| JP | 11-076211 | 3/1999 |
| JP | 11-164825 | 6/1999 |
| JP | 11-164825 A | 6/1999 |
| JP | 2000-237172 | 9/2000 |
| JP | 2001-161815 | 6/2001 |
| JP | 2001-515377 | 9/2001 |
| JP | 2001-524343 | 12/2001 |
| JP | 2002-000588 A | 1/2002 |
| JP | 2002-000696 | 1/2002 |
| JP | 2002-503119 A | 1/2002 |
| JP | 2002-186599 A | 7/2002 |

* cited by examiner

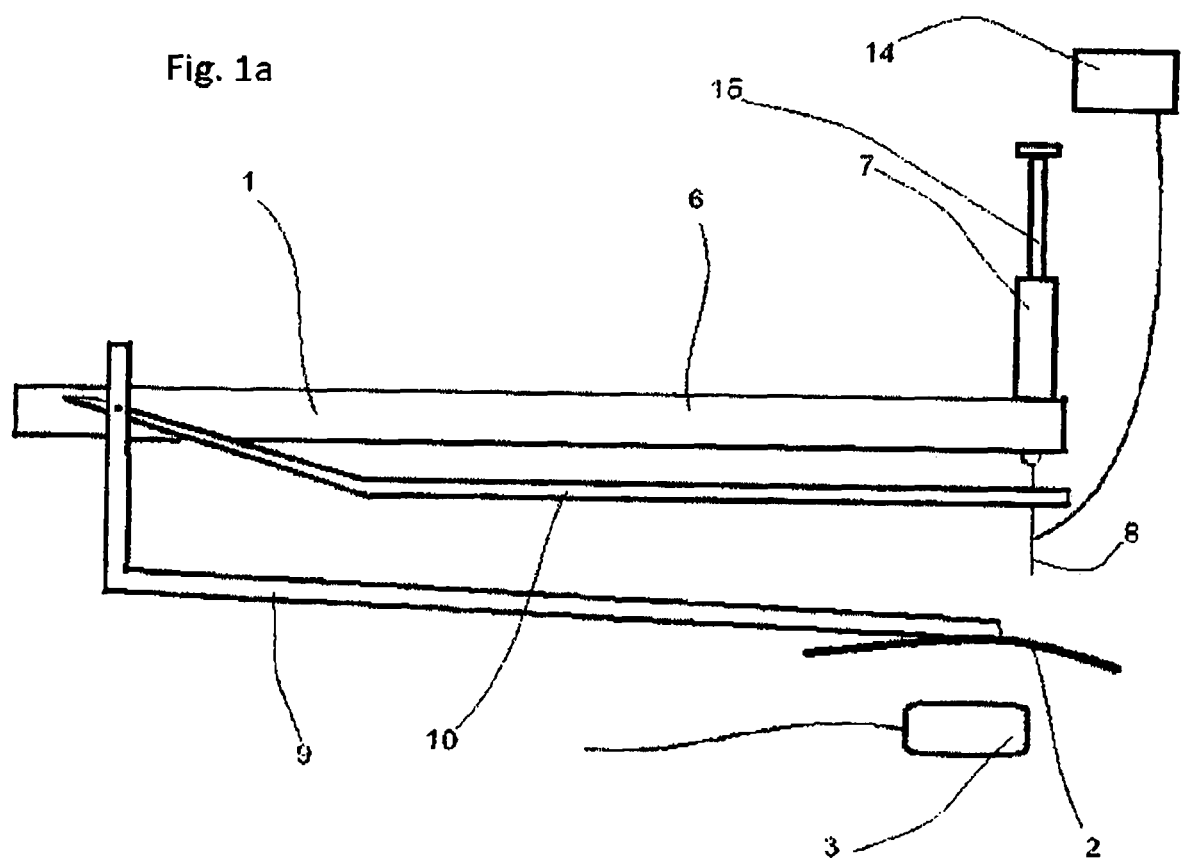

MEANS AND METHOD TO GIVE INJECTIONS WITH LITTLE OR NO PAIN

STATEMENT REGARDING FEDERALLY SPONSORED RESEARCH OR DEVELOPMENT

Not Applicable

THE NAME OF THE PARTIES TO A JOINT RESEARCH AGREEMENT

Not applicable.

INCORPORATION-BY-REFERENCE OF MATERIAL SUBMITTED ON A COMPACT DISC

Not Applicable

CROSS-REFERENCE TO RELATED INVENTION

This application is a continuation of U.S. patent application Ser. No. 12/590,658, filed Nov. 12, 2009, the contents of which are incorporated by reference in their entirety.

BACKGROUND OF THE INVENTION

The goal of the invention is to disclose a means, an injecting device 1, and a method of injection that reduces or altogether prevents the pain associated with injection. It has been shown that applying electric current can eliminate or alleviate certain chronic pain The Transcutaneous Electrical Nerve Stimulation (TENS) appliance makes use of this phenomenon and is currently used for this reason. This inventor has discovered that applying electricity to the vicinity of the injection site decreases or prevents the perception of pain of injection. This inventor has also discovered that physically stimulating the body near the site where electricity is applied lowers the uncomfortable perception of the shock of electrical current passing through the body. It also allows a more comfortable toleration of higher electrical voltages in the vicinity of the injection site. The higher voltage in turn provides a more profound temporary local anesthesia, and therefore, allows a better chance of a more comfortable or totally pain-free injection.

Furthermore, it was discovered by this inventor that post-injection soreness is minimized with the application of electricity to the vicinity of injection site in conjunction with an injection.

Furthermore, it is known that tapping, or otherwise physically stimulating the skin near the injection site at the same time as an injection lowers or altogether prevents the pain of injection. This phenomenon is used in this invention to further decrease or prevent the pain of injection. Even though tapping the skin is effective in preventing injection pain, it may be insulting to some recipients as it resembles slapping the recipient. A mechanized tapping device disclosed herein solves this problem.

The present invention also makes use of the fact that a rapid needle penetration is less painful than a slow one to further reduce the pain associated with an injection.

BRIEF SUMMARY OF THE INVENTION

Use is made of sensation of electrical shock and physical stimulation of the skin near the injection site to effect pair less or near painless injections.

BRIEF DESCRIPTION OF THE SEVERAL VIEWS OF THE DRAWINGS

The characteristics of the present invention will be better understood by reading the following description, given purely by way of example, and with reference to the accompanying drawings, in which:

FIG. 1a illustrates an injecting device which mechanically taps near the injection site and can actuate a rapid needle penetration into the skin.

DETAILED DESCRIPTION OF THE INVENTION

A preferred method to obtain painless or near painless needle 8 penetration is disclosed to be in the following manner: Applying electric current using a TENS device simultaneously with tapping the injection site for 30 to 60 seconds at a rate of about one strike per second, followed by a rapid needle 8 penetration into the skin 2.

Figure 3:
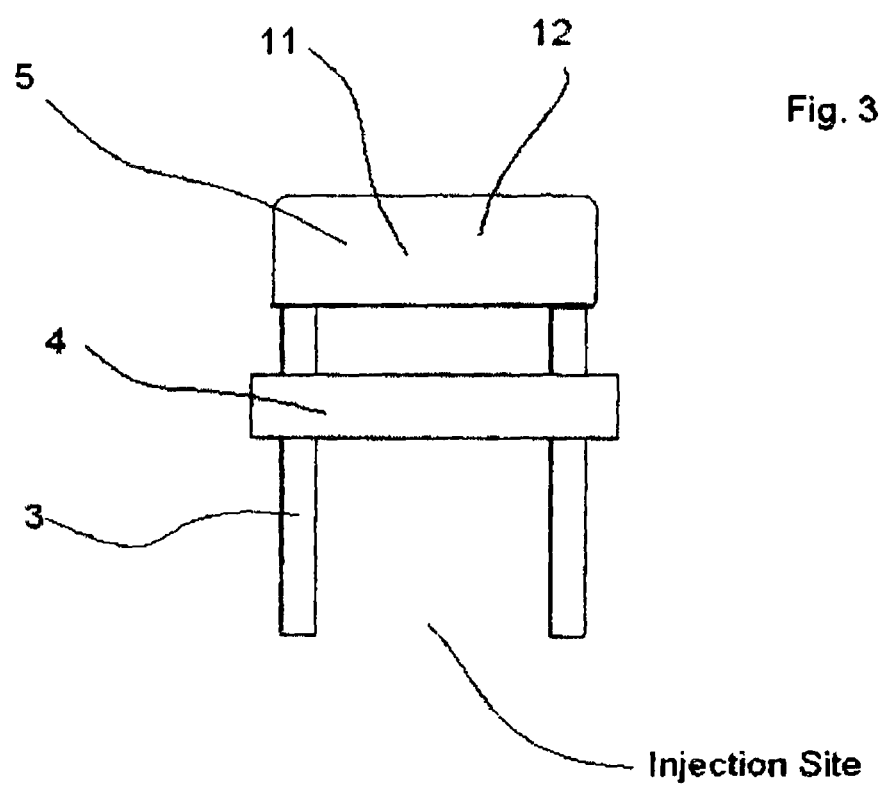
FIG. 3 shows 2 electrodes being grouped by a retaining means to facilitate placing the electrodes in contact with the skin of the injection recipient. It also shows a vibrating or shaking mechanism attached to the retaining means.

In order to facilitate to administer a painless injection, an electric source such as a TENS device is electrically attached to at least 2 electrodes 3, physically held near each other through a retaining means 4 that can bring in contact with the recipient's skin 2 said at least two electrodes 3 with ease, FIG. 3. After the application of electricity through the contact of electrodes 3 with the skin 2 for the required time, the injection is administered manually with minimal or no pain.

Figure 4:
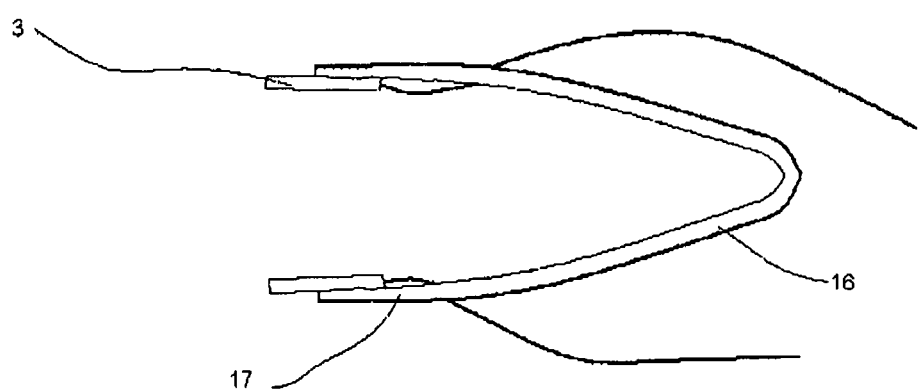
FIG. 4 shows a grip with accompanying electrodes to assist in grasping a layer of soft tissue, applying anesthetic electricity, and manually or mechanically administering an injection.

It is common to grasp soft tissue (skin and underlying tissue) firmly and administer an injection in the layer of soft tissue that is so grasped. In a specific example of the invention, said retaining means 4 is in the form of a grip 16 with at least 2 fingers 17, FIG. 4. At least one said electrode 3 is positioned on each of at least 2 said fingers 17. This feature will allow one to administer an injection into a layer of soft tissue while reducing or preventing the pain associated with the injection.

Figure 7:
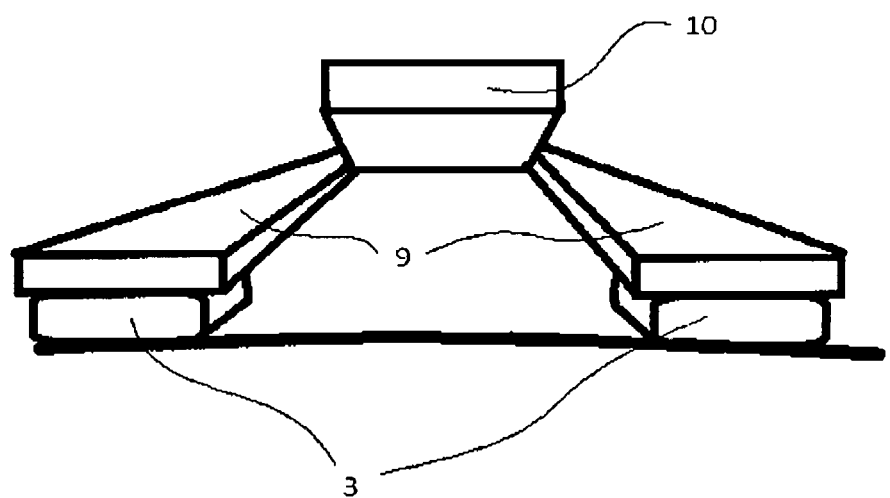
FIG. 7 is another view of the retainer and tapper of FIG. 1A, the retainer holding a plurality of electrodes.

In a specific example of the invention, in order to further prevent the pain of injection, said retaining means 4 also comprises a plurality of physical stimulators 5, FIG. 3 and FIG. 7. After application of electricity and eliciting a plurality of sensations around the c injection site for a required period of time, the injection is administered manually with minimal or no pain.

Figure 6:
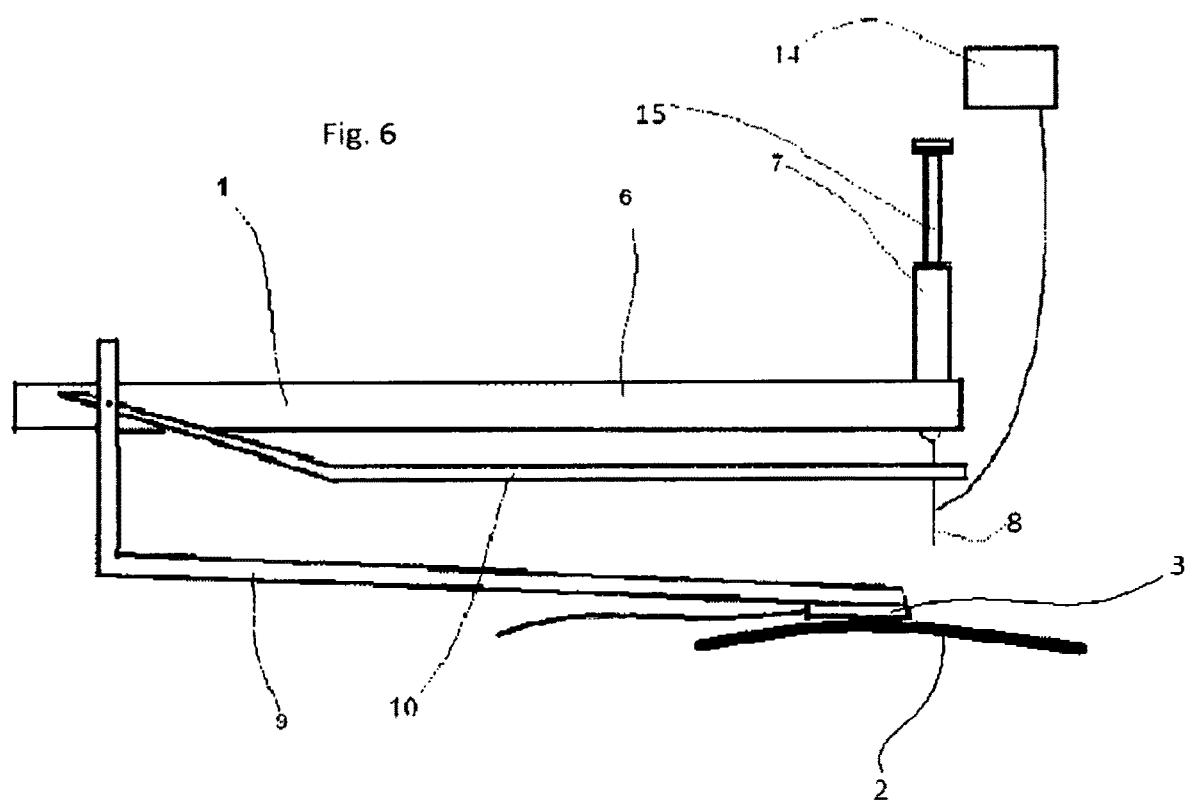
FIG. 6 illustrates the injection device of FIG. 1A with the positioning means holding the electrode.

In a related example of the invention, an injecting device 1 is disclosed to reduce or prevent the pain of injection comprising: A) a propeller 6 which holds a syringe 7 or a syringe needle 8 securely for skin 2 penetration and when actuated, rapidly moves said syringe needle 8 so that it penetrates the recipient's skin 2, and B) a plurality of electrodes 3 that can come in contact with the body of the recipient of the injection, in order to transmit an electric current to the skin 2, in the vicinity of the injection site, at least before, during, or after the needle 8 penetration, FIG. 1a and FIG. 6.

In a specific example of the invention, said injecting device 1 further comprises a plurality of physical stimulator 5 which elicit a plurality of sensations one or more times around the injection area at least before, after, or simultaneously with the penetration of the injection needle 8 into the skin 2, FIG. 1a.

In a specific example of the invention, said injecting device 1 further comprises a positioning means 9 to correctly position said device with respect to the recipient injection site so that said needle 8 will penetrate at a correct angulation and travel a correct distance into the recipient's soft tissue.

In a specific example of the invention, said electrodes 3 are in the form of pads.

In a specific example of the invention, said needle 8 forms one of the electrodes 3.

In a specific example of the invention, a TENS device supplies electricity to the skin, adjacent to the injection site.

In a specific example of the invention, the electrical current is Intermittent at a variable or constant frequency.

In a specific example of the invention, said electrodes 3 are electrically conductive rigid or semi-rigid means, physically attached to said injecting device 1, to provide ease of use of said injecting device 1. This way, said electrodes 3 need not be attached separately to the skin 2.

In a specific example of the invention, said electrodes 3 are physically attached to said positioning means 9.

An injecting device 1 is disclosed to reduce or prevent the pain of injection comprising: A) a propeller 6 which holds syringe 7 or a syringe 7 needle 8 securely for skin 2 penetration and when actuated, rapidly moves said syringe's 7 needle 8 so that it penetrates the recipient's skin 2, and B) a plurality of physical stimulators 5 which elicit a plurality of sensations one or more times around the injection area at least before, after, or simultaneously with the penetration of the injection needle 8 into the skin 2, FIG. 1a.

In a specific example of the invention, at least one of said physical stimulators 5 is an applicator (not shown), such s a spraying means, of a cooling agent, such as 1.1.1.2 tetrafluoroethane, at the vicinity of the injection site before, during, and/or after injection to further relieve the pain associated with an injection.

In a specific example of the invention, at least one of said physical stimulators 5 is a tapper 10 which taps one or ore times around the injection area at least before, after, or simultaneously with the penetration of the injection needle 8 into the skin 2.

In a specific example of the invention, at least one of said physical stimulators 5 is a shaking mechanism 11 that shakes the tissues around the injection area one or more times at least before, after, or simultaneously with the penetration of the injection needle 8 into the skin 2.

In a specific example of the invention, at least one of said physical stimulators 5 is a vibrating mechanism 12 that vibrates the tissues around the injection area one or more times at least before, after, or simultaneously with the penetration of the injection needle 8 into the skin 2.

In a specific example of the invention, at least one of said physical stimulators 5 is an applicator of a cooling substance, in the form of a solid, liquid, or gas, to the vicinity of the injection site.

In a specific example of the invention, at least one of said physical stimulators 5 is an applicator of heat radiation or a heating substance in the form of a hot solid, liquid or gas (such as a spraying means) to the injection site.

Figure 1B:
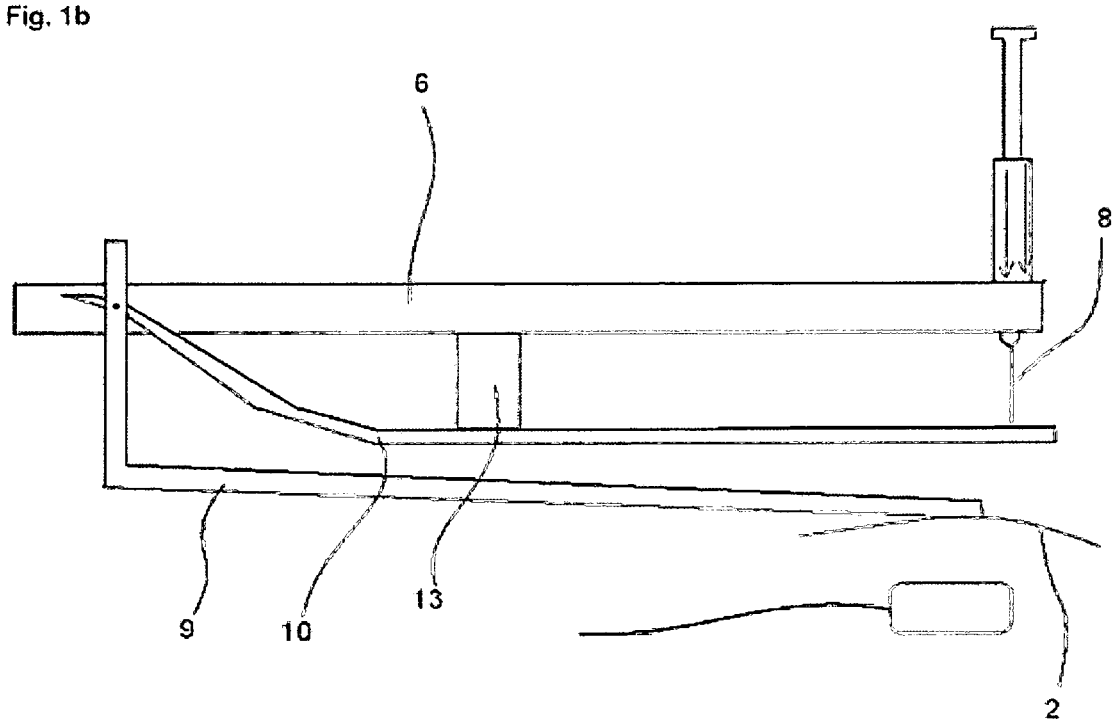
FIG. 1b shows a restrainer that prevents needle penetration prematurely before the adequate initial physical stimulation. It also shows the direction of the motion of the syringe to be generally parallel to the needle.

Even though many variations are possible within the scope of the invention, FIG. 1b shows a variation in which the propeller 6 and the tapper 10 move more or less vertically in tandem. A restrainer 13 limits the downward movement of said propeller 6 so that said needle 8 does not reach the recipient's skin 2 positioned under said injecting device 1. After a few taps produced by the rapid downward movement of said tapper 10 and said propeller 6, said restrainer 13 is removed allowing the further downward movement of said propeller 6 and the penetration of said needle 8 into the patient's skin 2.

In a specific example of the invention, the frequency of physically stimulating the tissue around the injection site is dependent on the frequency of the electrical current supplied by said electrodes 3.

Also disclosed, is a method of painless or near painless injection as follows: A) Applying a plurality of electrodes 3 to the body of the recipient of an injection so as to transmit an electrical current to the skin 2 in the vicinity of the injection site, before, during, and/or after the injection, and/or B) striking, shaking, vibrating, applying heat or cold, or otherwise physically stimulating the injection area before, during, and/or after the injection.

In a specific example of the invention, said tapper 10 is part of said propeller 6. Said needle's 8 position is adjustable with respect to said propeller 6. For example, said needle 8 can be positioned so that it cannot reach the recipient's skin 2 during the initial one or more strikes of said tapper 10. Said needle 8's position can then be adjusted on said propeller 6 so that when said propeller 6 travels its full distance, said needle 8 reaches and penetrates the recipient's skin 2 a certain predetermined length, FIG. 1a.

In a specific example of the invention, as a safety mechanism, said needle 8 acts as an electrical probe and is electrically connected to a sensor 14 to sense any change in the electrical environment said needle 8 is in. Since the electrical environments outside and inside the body are different, the sensor 14 can verify whether or not said needle 8 penetrated the recipient's skin 2. This proves important since, when using said injecting device 1, the recipient does not feel the needle 8 penetration, he cannot ascertain on his own whether the medicine entered his or her body or whether it poured useless outside the body. For example, without said needle 8 penetration, said sensor 14 alerts the recipient not to press the plunger 15 on said syringe 7 and not to waste the life-saving medicine contained in said syringe 7.

Figure 5:
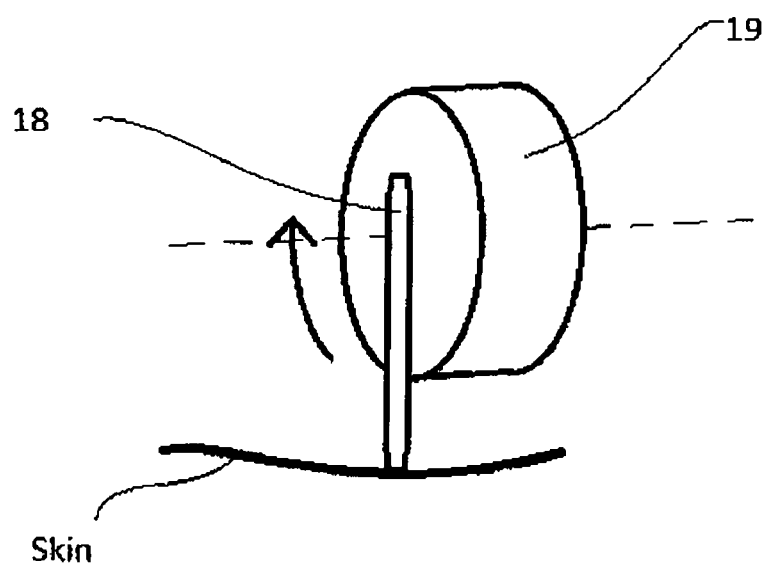
FIG. 5 shows a rod rotating around an axis striking the skin of a recipient of an injection at or in the vicinity of an injection site.

Said tapper 10 can be fashioned in many ways. For example, it can be a semi-rigid rod that moves up and down and strikes the recipient's skin 2. It can be a spring pressed and released one or more times, striking the skin 2. It can be a flexible, inflatable membrane that, when inflated strikes the recipient's skin 2. Or it can be a flexible, rotating, rod attached to a wheel that strikes the skin 2 when rotating around an axis, FIG. 5. Many other variations are possible in designing of said tapper 10 as available to one skilled in the art.

In a specific example of the invention, said retaining means 4 is attached to said injecting device 1.

In a specific example of the invention, said retaining means 4 is in the form of a said grip 16 and is attached to said injecting device 1. Therefore, even though the administration of an injection is mechanized, said needle 8 can penetrate a layer of soft tissue grasped between said fingers 17 of said grip 16.

In a specific example of the invention, at least one of the following: the actuation and movement of said propeller 6, the vibration of said vibrating mechanism 12, the shaking action of said shaking mechanism 11, the action of said applicator of heat radiation, the action of said applicator of heating substance, the action of said applicator of cooling substance, or the movement of said tapper 10 is motorized.

In a specific example of the invention, a computer controls the duration and sequence of at least one of the following: the actuation and movement of said propeller 6, the vibration of said vibrating mechanism 12, the shaking action of said shaking mechanism 11, the action of said applicator of heat radiation, the action of said applicator of heating substance, the action of said applicator of cooling substance, applying electricity to a plurality of said electrodes 3, and the movement of said tapper.

As said before, physical stimulation of the body along with passing electrical current through the body masks the sensation of the electrical shock. This discovery is also helpful in the traditional use of the TENS appliance or other instances where applying electrical shock is beneficial. With the application of physical stimulation, the perception of electrical shock of higher voltages is more comfortably tolerated. Higher voltages result in a better relief of chronic pain to the sufferer.

Figure 2:
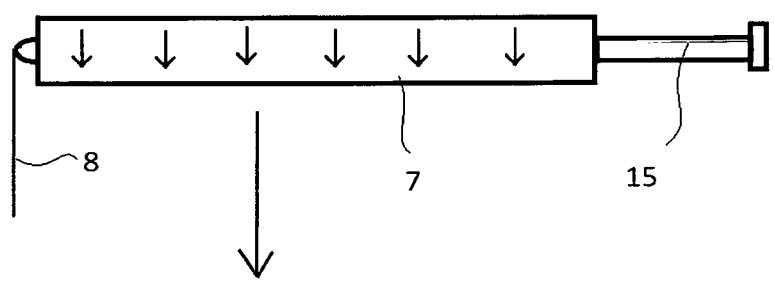
FIG. 2 illustrates a revised syringe design that prevents the escape of the syringe contents from the needle during the initial tapping and shaking of the syringe.

Also disclosed is a preferred design of a syringe 7 with its needle 8 extending out of said syringe 7 at about a perpendicular angle, FIG. 2. This helps to contain the contents of said syringe 7 during the primary shaking and/or tapping of the skin 2 before said needle 8 penetrates the skin 2 because the inertia of the contents presses the contents against the body of said syringe 7 where there is no needle 8 orifice for the contents to escape. The arrow in FIG. 2 shows the general direction of the syringe 7 motion. Whereas in the traditional case where said needle 8 exits straight out of said syringe 7, the inertia of the contents adds pressure on the contents to exit said needle 8 prematurely before said needle 8 penetrates into the skin 2, FIG. 1*b*.

There is a new method of injecting medicine without the use of a needle. This method relies on applying a jet of gas to push a medicament into the skin. Applying said electrodes 3 and/or physically stimulating the skin at least before, during, or after the needle-less injection will minimize or prevent any discomfort associated with this technique as well. Even though the teachings disclosed in this invention generally refer to an injection through a needle, they equally relate to the new needle-less injection technique as well.

Applying electricity to the skin 2 together with or without physically stimulating the skin induces a local anesthesia which will allow certain surgical procedures as well as performing tattoos comfortably without the use of chemical anesthetics.

One skilled in the art will appreciate that the present invention can be practiced by other than the described embodiments, which are presented here for purposes of illustration and not of limitation, and the present invention is limited only by the claims that follow.

What I claim is:

1. A device for reducing or preventing pain associated with an injection into an injection site comprising:
    a) A tapper configured to repeatedly tap a recipient's soft tissue,
    b) a plurality of electrodes that apply electricity to the tissue, and
    c) a retainer that holds said plurality of electrodes and said tapper, said retainer being configured to position said device with respect to the injection site prior to said injection.

2. The device according to claim 1 wherein said tapper rotates around an axis.

3. The device according to claim 1, wherein the retainer is configured to position said tapper at a predefined distance and angulation with respect to skin of the recipient.

4. The device according to claim 1 wherein said tapper is configured to repeatedly tap the recipient's soft tissue so as to contact the tissue at least two separate times.

5. The device according to claim 1 wherein a frequency of said tapping is selected based at least in part on a frequency of an electrical current supplied by said plurality of electrodes.

6. The device according to claim 3, wherein the predefined distance and angulation are such that the tapper must travel at least as far as the predefined distance to tap on the tissue.

7. A method of painless or near painless injection, comprising applying electricity through a plurality of electrodes to an injection-recipient's soft tissue, positioning, with a retainer prior to the injection, a tapper relative to the recipient's soft tissue, and tapping on the tissue with the tapper, wherein the tapper is held by the retainer.

8. The method according to claim 7 wherein said tapper rotates around an axis.

9. The method according to claim 8, wherein said tapping is performed before the injection.

10. The method according to claim 7 wherein at least one of said electrodes is physically attached to said retainer.

11. The method according to claim 7 wherein said retainer comprises at least one of said electrodes.

12. A method of painless or near painless injection comprising:
    a. applying electricity through a plurality of electrodes to an injection-recipient's soft tissue;
    b. tapping on the tissue so as to contact the tissue at least two separate times;
    c. stopping said tapping before administering said injection; and
    d. administering said injection.

13. The method according to claim 12, wherein said tapping mitigates an electric shock sensation in the soft tissue generated by at least one of said plurality of electrodes.

14. The method according to claim 12, wherein said tapping is performed on an injection site.

15. The method according to claim 12, wherein said tapping is performed during or after said applying of electricity.

16. The method according to claim 12, wherein said tapping is performed by a tapper which is held by a retainer, wherein said retainer also holds said plurality of electrodes, and wherein said retainer positions said tapper and said plurality of electrodes with respect to an injection site prior to said injection.

17. The method according to claim 12, wherein a frequency of said tapping is selected based at least in part on a frequency of an electrical current supplied by said electrodes.

18. The method according to claim 12, wherein said electricity is generated by a TENS device.

19. The method according to claim 16, wherein said tapper rotates around an axis.

20. A method of reducing pain of an injection into a recipient's soft tissue comprising the steps of:
   a. grasping said soft tissue with a grip, said grip comprising at least two fingers, each finger comprising an inner surface and an outer surface, wherein the grasping includes holding said outer surfaces of said at least two fingers;
   b. applying electricity to said soft tissue through a plurality of electrodes; and
   c. tapping on the soft tissue;
wherein at least one of said plurality of electrodes is positioned on said inner surface of at least one of said at least two fingers of said grip.

\* \* \* \* \*